(12) United States Patent
Ulmer et al.

(10) Patent No.: US 8,450,103 B2
(45) Date of Patent: May 28, 2013

(54) METHOD OF DERIVATISING AN ANALYTE FOR SUBSEQUENT DETECTION THROUGH A NUCLEIC ACID BASED SENSOR

(75) Inventors: Jens Ulmer, Heidelberg (DE); Michael Hulko, Stuttgart (DE); Ingeborg Hospach, Stuttgart (DE); Gabriele Nelles, Stuttgart (DE)

(73) Assignee: Sony Corporation, Tokyo (JP)

( * ) Notice: Subject to any disclaimer, the term of this patent is extended or adjusted under 35 U.S.C. 154(b) by 703 days.

(21) Appl. No.: 12/574,458

(22) Filed: Oct. 6, 2009

(65) Prior Publication Data

US 2010/0089769 A1  Apr. 15, 2010

(30) Foreign Application Priority Data

Oct. 6, 2008 (EP) .................................... 08017509

(51) Int. Cl.
*C12M 1/34* (2006.01)
*C12M 3/00* (2006.01)
*C12M 1/00* (2006.01)

(52) U.S. Cl.
USPC ................... 435/287.2; 435/283.1; 435/287.1

(58) Field of Classification Search
USPC ........................ 435/6, 6.1, 283.1, 287.1, 287.2
See application file for complete search history.

(56) References Cited

U.S. PATENT DOCUMENTS

| | | | | |
|---|---|---|---|---|
| 5,043,166 A | * | 8/1991 | Barenholz et al. | 424/450 |
| 5,607,565 A | * | 3/1997 | Azarnia et al. | 204/403.09 |
| 6,355,423 B1 | * | 3/2002 | Rothberg et al. | 435/6.16 |
| 2002/0102568 A1 | * | 8/2002 | Usman et al. | 435/6 |
| 2004/0191801 A1 | * | 9/2004 | Heeger et al. | 435/6 |
| 2007/0254282 A1 | * | 11/2007 | Willner et al. | 435/6 |

FOREIGN PATENT DOCUMENTS

WO    WO 2007/120299 A2    10/2007

OTHER PUBLICATIONS

Anna Collén, et al., "Genetically engineered peptide fusions for improved protein partitioning in aqueous two-phase systems Effect of fusison localization on endoglucanase I of *Trichoderma reesei*", Journal of Chromatography A, 910 (2001) 275-284, XP-00250811.
Pradip K. Banerjee, et al., "Physicochemical Property Modification Strategies Based on Enzyme Substrate Specificities I: Rationale, Synthesis, and Pharmaceutical Properties of Aspirin Derivatives", Journal of Pharmaceutical Sciences, Dec. 1981, vol. 70, No. 12, 1299-1303, XP-009103213.
Naveen K. Navani, et al., "Nucleic acid aptamers and enzymes as sensors", Current Opinion in Chemical Biology, 2006, 10:272-281.
Gyeong Sook Bang, et al., "A novel electrochemical detection method for aptamer biosensors", Biosensors Bioelectronics, vol. 21, No. 6, Dec. 15, 2005, pp. 863-870.
Marcela C. Rodriguez, et al., "Aptamer biosensor for label-free impedance spectroscopy detection of proteins based on recognition-induced switching of the surface charge", Chemical Communications, No. 34, Sep. 14, 2005, pp. 4267-5269, XP009114460.
Ye Tian, et al., "DNAzyme amplification of molecular beacon signal", Talanta—Nanoscience and Nanotechnology. vol. 67, No. 3, Sep. 15, 2005, pp. 532-537, XP005047824.

* cited by examiner

*Primary Examiner* — Robert T. Crow
(74) *Attorney, Agent, or Firm* — Oblon, Spivak, McClelland, Maier & Neustadt, L.L.P.

(57) ABSTRACT

A method of derivatising an analyte for subsequent detection through a nucleic acid based sensor and a sensor based thereon.

19 Claims, 6 Drawing Sheets

Scheme 4
*Receptor molecule configuration*

1. Enzyme domain (inactive)
2. Communication domain
3. Ligand binding domain
(non bound state)

Activation through ligand binding →

1. Enzyme domain (active)
2. Communication domain
3. Ligand binding domain
(bound state)

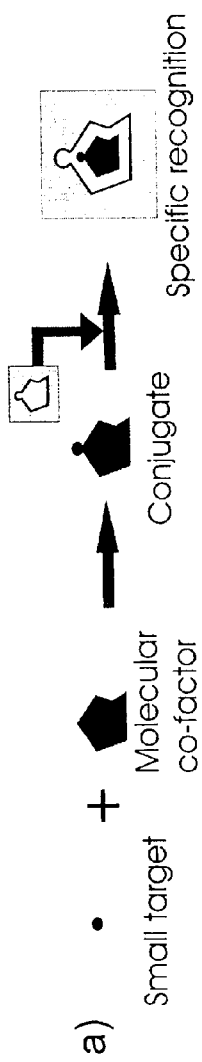
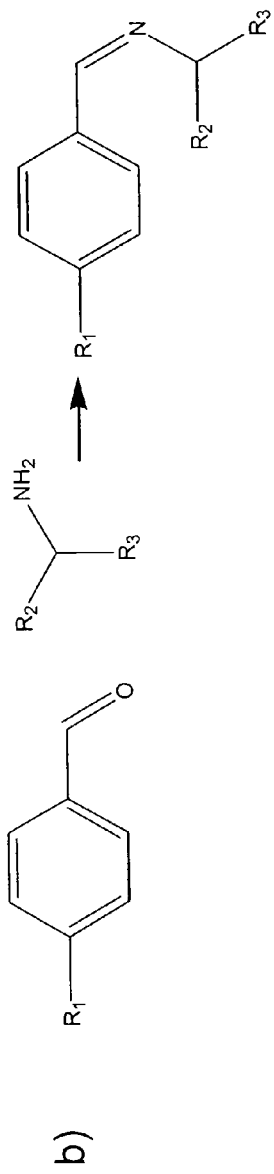
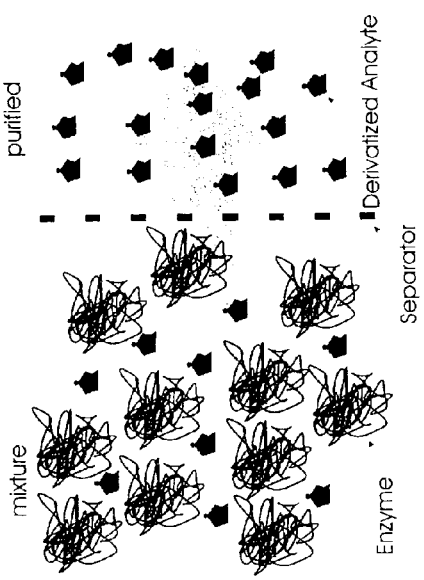
Fig. 1

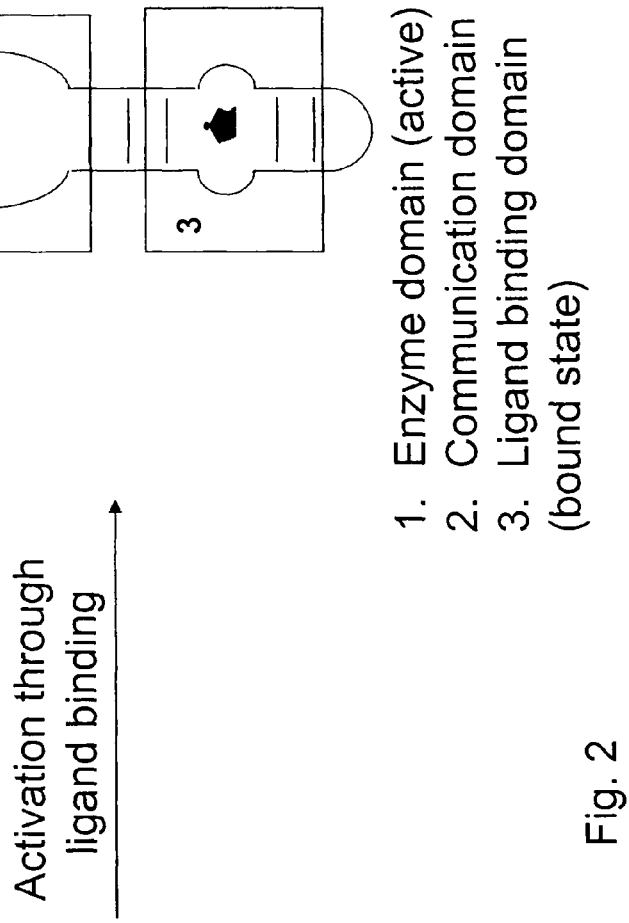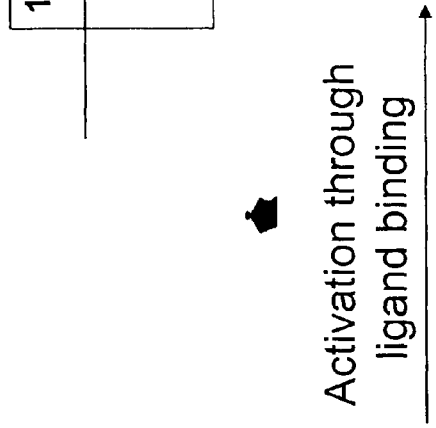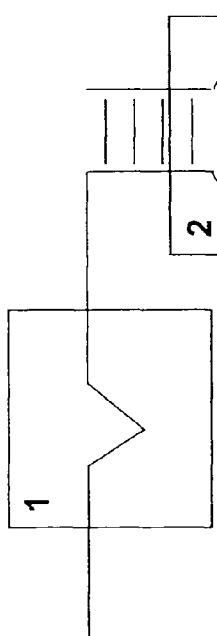
Fig. 2

METHOD OF DERIVATISING AN ANALYTE FOR SUBSEQUENT DETECTION THROUGH A NUCLEIC ACID BASED SENSOR

CROSS-REFERENCE TO RELATED APPLICATIONS

This application claims priority to EP 08 017 509.4, filed Oct. 6, 2008, which is hereby incorporated by reference.

BACKGROUND OF THE INVENTION

1. Field of the Invention

The present invention is directed to a method of derivatising an analyte for subsequent detection through a nucleic acid based sensor, and to a sensor based thereon.

2. Description of the Related Art

Since the introduction of in vitro evolution principles (Systematic Evolution of Ligands by Exponential enrichment, SELEX) in the late 1980, a vast number of synthetically derived nucleic acids have been established resembling a high specificity and affinity against a huge variety of target molecules. This class of molecules (hereinafter Functional Nucleic Acids, FNAs) recently has attracted much interest in fields like analysis for environmental monitoring, diagnosis, drug discovery and therapy to combat diseases.

In general sensors consist of two major units: a signal receptor unit and a signal transducing unit. Chemical receptor units comprise a synthetically derived material that interacts with the sample or the analyte. Low limits of detection are achieved by strong and direct chemical or physical interaction between the analyte and the receptor material. On the other hand biological receptor units comprising biological derived materials show a specific detection by the specific chemical or physical interaction between the biological receptor and the analyte molecule. The interaction between the receptor material and the analyte is measured as a change in various physical or chemical properties and is processed inside the transducing unit. This change is converted to a measureable signal correlating linear with the concentration of analyte molecules. It can be realized by changes of various properties like conductivity/resistivity, capacity, current, potential, light absorption and fluorescence.

Like antibodies or enzymes, FNAs have been used as highly specific biological receptor unit in bio-sensor applications against targets like peptides, proteins, DNA, RNA or organic and inorganic molecules. In principle, for FNA's exists no limitations concerning structure, size or status of the envisioned target molecule and one can evolve FNA's against analytes including those for which antibodies are difficult to obtain (metal ions, toxins or volatile compounds). Moreover, FNA based sensors can be established for demands where protein receptors are ineffectual (elevated temperature, non aqueous or complex environments).

FNA based sensors had shown in the past a remarkable selectivity. For example aptamers were found to selectively distinguish theophylline and caffeine by a factor of 10,000 where the only difference is a single methylene group inside the two molecules (U.S. Pat. No. 5,580,737). A modular designed FNA where the recognition domain is separated from the signal generating domain, allows more freedom in sensor design. Thereby a plurality of target molecules can be detected with the same sensing principle (electrical, optical, calorimetrical or gravimetrical). The de novo in vitro design of FNA based bio-sensor receptor units makes them exceedingly useful to determine and sense components out of complex environments with high specificity.

Beside their remarkably advantages, FNAs as a natural occurring material show also some major disadvantages. They are normally subjected to considerable degradation under physiological conditions which can be inhibited by capping or implementation of non-natural nucleotides like spiegelmere, fluorinated ribosyl residues and phosphorthioate. This makes them more resistive to hydrolytic or enzymatic degradation and potentially more useful for in vitro and in vivo sensor applications.

In general, for trace analysis of biological samples a signal amplification step is essential to increase the sensitivity. In case for FNAs as recognition element, DNAzymes proved to show a multiple turnover activity, which also can amplify readout signals. After activation through the analyte it can continuously activate previously inactive reporter molecules (e.g. stem-loop forming DNA).

This leads to a significant signal enhancement because each analyte molecule can create many reporter molecules.

Through these FNA properties in combination with transduction principles (electrical, optical, calorimetrical or gavimetrical) employing FNAs as recognition elements, peptides, proteins, DNA, RNA or organic and inorganic molecules were detected out of complex environments with high specificity and sensitivity.

A number of disadvantages and shortcomings limit the usage of FNAs as recognition element for sensing applications and trace analysis in complex environments for small, charged or nonpolar organic or inorganic molecules:

Target evaluation of FNAs is always performed using the SELEX process wherein a specific target molecule is immobilized onto a solid phase and a library of FNAs comprising a complexity of about $10^{14}$ randomly mutated molecules are used to select for a specific receptor-target interaction. However, recognition of target molecules dramaticaly worsen with the size and chemical nature of the target analyte making it almost impossible to get highly specific FNAs for small organic and inorganic compounds.

Another limitation is based on the fact that FNA can degrade rapidly under physiological condition. This degradation limits the time of operation of FNAs as the recognition unit in bio-sensors when operated under conditions where RNA/DNA can be hydrolyzed or is subjected to enzymatic decomposition. To overcome this shortcoming non natural nucleotides like spiegelmere, fluorinated ribosyl residues and phosphorthioates are commonly used. This implies the usage of complicated and expensive synthesis methodologies and the results do not meet the requirements necessary for selective and sensitive sensor applications.

In prior art, readout of DNAzyme amplified molecular beacon signal events occurs via fluorescent reporter molecules. This requires complex illumination, optics and detection systems, which therefore cannot easily be implemented into small devices.

BRIEF SUMMARY OF THE INVENTION

Accordingly, it was an object of the present invention to provide for improved methods for increasing the sensitivity of nucleic acid based sensors, especially for small analyte molecules.

These objects are solved by a method of derivatising an analyte for subsequent detection of said analyte through a sensor based on specific recognition of said derivatised analyte by a nucleic acid, said method comprising:

providing, in any order, an analyte having a first functional group, and a derivatisation agent having a second functional group, wherein said first and said second functional group are capable of reacting with each other to form a bond between said analyte and said derivatisation agent, said derivatisation agent further having a substituent allowing for base stacking or hydrogen bonding between said derivatisation agent and said nucleic acid, allowing said derivatisation agent and said analyte to react to form a derivatised analyte.

In one embodiment, said analyte is a molecule having a molecular weight in the range of from 1-500 Da, preferably in the range of 10-300 Da and more preferably in the range of 50-250 Da.

In one embodiment, wherein said first functional group is selected from phenyls, alcohols, ketons, aldehydes, carboxylic acids, carboxylic esters, ethers, epoxides, thiols, amines, amides and halides.

In one embodiment, said second functional group is selected from aldehydes, isothiocyanates, activated esters, maleimides, iodoacetamides, phenylmercury groups, triazines, hydrazines, hydroxylamines, and dialdehydes.

In one embodiment, said substituent is selected from pyridines, purines, aromatic amines, amides, carboxylic acids, peptides containing tyrosine, tryptophane and/or phenylalanine.

In one embodiment, said derivatised analyte has a molecular weight in the range from 50-10,000 Da, preferably in the range from 100-5,000 Da and more preferably in the range of 250-2,000 Da.

In one embodiment, the method according to the present invention further comprises the step of detecting said derivatised analyte by means of a sensor based on specific recognition of said derivatised analyte by a nucleic acid.

In one embodiment, the method according to the present invention further comprises the step of subjecting said derivatised analyte, prior to detection, to an exclusion process whereby molecules having a molecular weight >10,000 Da are separated from said derivatised analyte, preferably by means of a semipermeable membrane allowing only molecules having a molecular weight <10,000 Da pass from a first side of said membrane to a second side of said membrane opposite said first side.

Objects of the present invention are also solved by a sensor for detection of an analyte, preferably a derivatised analyte produced by the method according to any of embodiments 1-8, said sensor being based on specific recognition of said analyte by a nucleic acid, said sensor comprising a detection compartment comprising:

a) a first nucleic acid being capable of specifically recognizing and binding an analyte, e.g. a derivatised analyte said first nucleic acid comprising an activatable enzyme domain, said enzyme domain, in an active state, having a site specific cleavage activity on nucleic acids, an analyte binding domain capable of specifically recognizing and binding an analyte, a communication domain linking said activatable enzyme domain and said analyte binding domain, wherein said activatable enzyme domain is activated from an inactive to an active state upon binding of said analyte to said analyte binding domain, b) a set of at least a first and second electrode attachable to a power supply, c) a second nucleic acid having a partially double stranded structure and comprising an intercalating, redox-active compound capable of binding to said second nucleic acid, which compound either is electrochemically detectable in its unbound form and is electrochemically not detectable in its bound form, or said compound is electrochemically detectable in its bound form and is electrochemically not detectable in its unbound form, wherein said second nucleic acid further comprises a cleavage site recognized by said enzyme domain of said first nucleic acid in its active state, and wherein, upon cleavage of said cleavage site, said intercalating, redox-active compound, when bound to said second nucleic acid, becomes released from said second nucleic acid.

In one embodiment, said first nucleic acid is a DNAzyme, preferably selected from 8-17 DNAzyme and 10-23 DNAzyme. As used herein, the term "DNAzyme", is meant to refer to catalytically active DNA. The term is used synonymously with "DNA enzyme". A review of such DNA enzymes (DNAzymes) can for example be found in S. W. Santoro, G. F. Joyce, Proc. Natl. Acad. Sci. USA, 94 (1997), 4262. The terms "8-17 DNAzyme" and "10-23 DNAzyme", as used herein, refer to DNAzymes as described in the aforementioned reference which is incorporated by reference. Such terms are therefore understood by someone skilled in the art.

In one embodiment, said second nucleic acid is a stem-loop forming DNA probe, preferably selected from nucleic acids having a sequence of 21 nucleotides and forming a stem loop structure, e.g. CCTGAGAGAGrArUGGGTGCAGG (SEQ ID NO: 2) wherein the cleavage site is highlighted with bold letters (r stands for the origin of the nucleotide, in this case RNA).

In one embodiment, said intercalating, redox-active compound is selected from methylene blue, cyanine derivatives, acridine derivatives, ethidium bromide, propidium iodine, hydroxystilbamidine derivatives, anthraquinone derivatives, bis-benzimide derivates like Hoechst 34580, 33258, 33342, ferrocenyl naphthalene diimide, daunomycine, anthraquinone disulfonic acid, $Co(bpy)_3^{3+}$, and $Co(phen)_3^{3+}$, wherein "bpy" is bipyridine and wherein "phen" is 1,10 phenanthroline.

In one embodiment, said sensor has one of the following configurations:

a) said first nucleic acid is bound to a surface of at least one of said electrodes, said second nucleic acid is in a solution covering, contacting or surrounding said surface, wherein, for detecting, a sample believed to contain an analyte is added to said solution;

b) said second nucleic acid is bound to a surface of at least one of said electrodes, said first nucleic acid is in a solution covering, contacting or surrounding said surface, wherein, for detection, a sample believed to contain an analyte is added to said solution;

c) said first and said second nucleic acid are in a solution covering, contacting or surrounding a surface of at least one of said electrodes, wherein, for detection, a sample believed to contain an analyte is added to said solution; or d) said first and said second nucleic acid are bound to a surface of at least one of said electrodes, wherein, for detection, a sample believed to contain an analyte is added so as to contact said surface.

In one embodiment, the sensor according to the present invention further comprises a separation compartment located upstream of said detection compartment and being separated from said detection compartment by a semipermeable membrane, allowing only molecules having a molecular weight <10,000 Da pass from said separation compartment to said detection compartment, said semipermeable membrane being a polymeric membrane, preferably a membrane made of one of cellulose, methylated cellulose, dextran, in particular crosslinked dextran, cellophane, polytetrafluoroethylen, polyamide, polyethersulfone, polypropylene or zeolites, aluminum oxide and combinations thereof.

The objects of the present invention are also solved by a method of detecting an analyte in a sample comprising the steps:
- providing, in any order, a sensor according to the present invention, and a sample containing an analyte, in particular a derivatised analyte according to the present invention,
- exposing said sensor to said sample, and
- measuring an electrochemical response, wherein the presence and magnitude of said electrochemical response is indicative of the presence and amount of said analyte in said sample.

The objects of the present invention are also solved by the use of the method of derivatising in accordance with the present invention, or of the method of detecting according to the present invention, or of the sensor according to the present invention, for medical and/or healthcare diagnosis, food quality testing, agricultural testing, security testing for explosives, toxins or harmful chemical substances, and/or occupational or environmental monitoring.

BRIEF DESCRIPTION OF THE DRAWINGS

FIGS. 1a, b and c show the specific recognition of a small analyte molecule ("small target") which has been derivatised by a derivatising agent ("molecular cofactor") through a nucleic acid (FIG. 1a, Scheme 1), a specific example of a derivatisation reaction (FIG. 1b, Scheme 2), and a size exclusion process in accordance with the present invention (embodiment of FIG. 1c, Scheme 3).

FIG. 2 (receptor molecular configuration, Scheme 4) shows an embodiment of a first nucleic acid in accordance with the present invention; the "ligand" in FIG. 2 may, for example, be a derivatised analyte produced by the method according to the present invention.

DETAILED DESCRIPTION OF THE INVENTION

Figure 3:
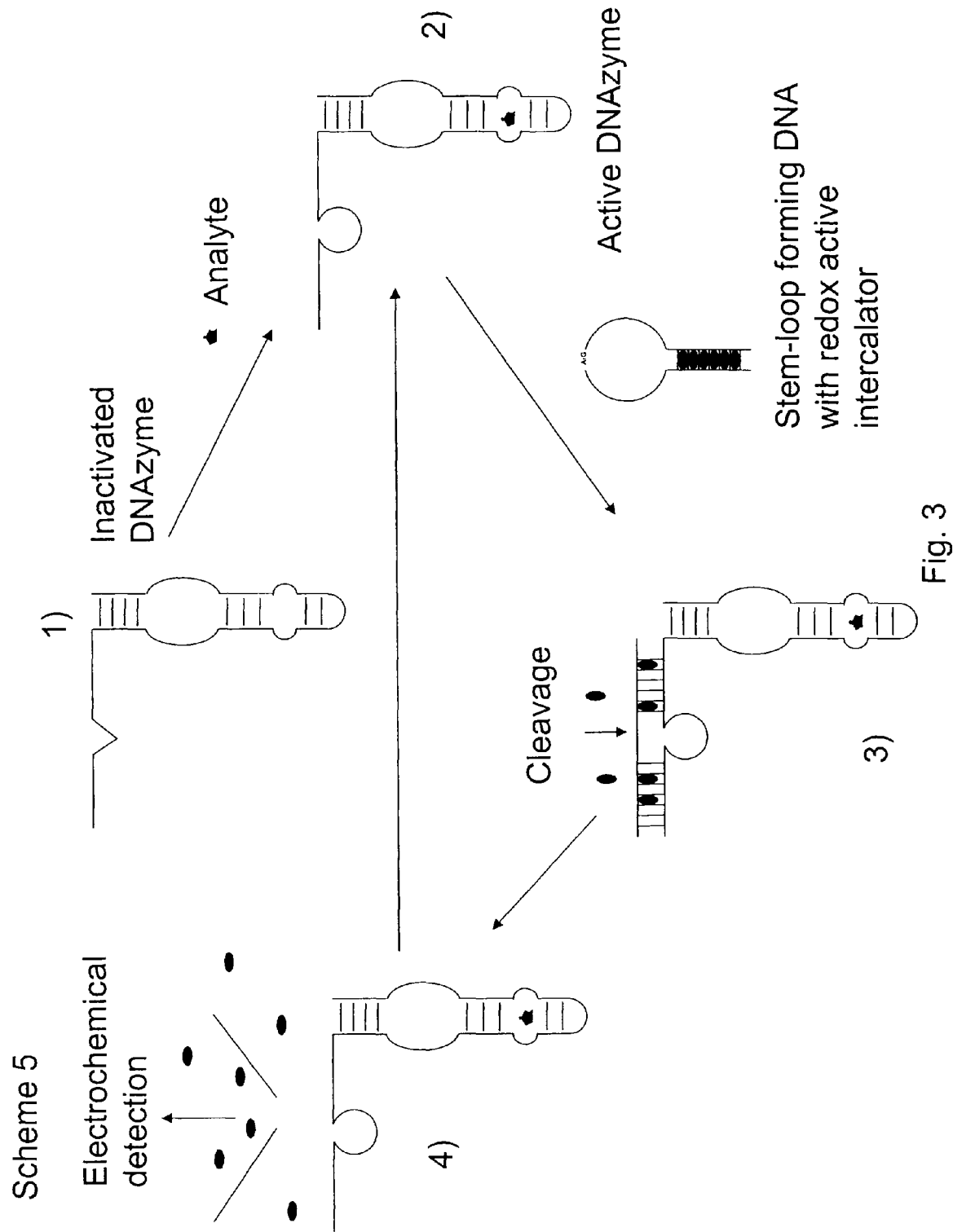
FIG. 3 (Scheme 5) shows a detection reaction using the first and second nucleic acid in accordance with the present invention; the first nucleic acid is a DNAzyme which becomes activated upon binding of an analyte, e.g. a derivatised analyte; the second nucleic acid is a stem-loop forming DNA comprising a redox active intercalator. The second nucleic acid becomes cleaved by the activated first nucleic acid, and the intercalator becomes released.

As used herein, the term "a sensor based on specific recognition of said analyte by a nucleic acid" is also herein sometimes referred to as a "functional nucleic acid based sensor" or "FNA based sensor".

The analyte in accordance with the present invention is preferably a "small molecule". The term "small molecule", as used herein, is meant to refer to a molecule having a molecular weight preferably in the range of from 1-500 Da, more preferably in the range from 10-300 Da and most preferably in the range of 50-250 Da.

Once the analyte has been derivatised in accordance with the present invention, its molecular weight comes to lie preferably in the range from 50-10,000 Da, more preferably in the range from 100-5000 Da and most preferably in the range of 250-2000 Da. Although such derivatisation processes are known with respect to antibody preparation, to the best knowledge of the inventors, such derivatisation has never been used in order to enhance the sensitivity of a nucleic acid based sensor.

In an embodiment of a sensor in accordance with the present invention, the first nucleic acid is capable of specifically recognizing and binding an analyte and comprises an analyte activatable enzyme domain, an analyte binding domain, capable of specifically recognizing and binding an analyte, and a communication domain linking said activatable enzyme domain and said analyte binding domain. Moreover, the sensor comprises a second nucleic acid which has a partially double stranded structure and comprises an intercalating, redox-active compound bound to said second nucleic acid. Preferably such second nucleic acid is a stem-loop forming DNA. The term "stem-loop forming DNA", as used herein, refers to a nucleic acid that is capable of reporting the presence or activity of specific nucleic acids in solution, and is capable of forming a stem-loop structure under defined conditions. In accordance with the present invention, the stem-loop forming DNA comprises an intercalating, redox-active compound and a cleavage site specifically recognized by the analyte activatable enzyme domain of the first nucleic acid. Upon cleavage of the cleavage site, the intercalating, redox-active compound bound to the stem-loop forming DNA, or, more generally, second nucleic acid is released into solution and becomes electrochemically detectable, or loses its detectability, depending on the set-up (see also FIGS. 4-6).

Preferred examples of the first nucleic acid are DNAzymes, and more preferably a sequence represented by 5'-GCGTC-CTTCAGAGAGAGTGGGTGCTTTTGCAC-CCAGGCTAGCTACAACGACTCT CTC-3' (SEQ ID NO: 1) where the bold letters represent the enzymatically active domain.

Preferred examples of the second nucleic acid in accordance with the present invention are stem-loop forming DNAs, or stem-loop forming DNA probes selected nucleic acids having a sequence of 21 nucleotides and forming a stem loop structure, e.g. CCTGAGAGAGrArUGGGTGCAGG-3' (SEQ ID NO: 2) wherein the cleavage site is highlighted with bold letters (r stands for the origin of the nucleotide, in this case RNA; see e.g. Tian Y., Mao C., Talanta 67 (2005), 532), which is incorporated by reference.

In general FNA based receptor units in accordance with the present invention can comprise natural or synthetic materials specified as follows:
RNA/DNA with natural or non-natural nucleotides, Aptamers, Ribozyme, Aptazymes, DNAzyme, PNA (Peptidic nucleic acid)

The conversion of small molecules by derivatizing agents into more perceptible molecules for the FNA recognition pathway is disclosed in this invention. This allows the detection of small molecules produced and emitted from various sources as solids, liquids, gases and mixtures thereof with sensors bearing FNA units as the central recognition element. Specific reactions can occur directly between the analyte molecules and the derivatization agent or it can be catalyzed by a third class of organic/inorganic molecule, peptide, enzyme, DNA/RNA. This derivatization also supports the transfer of target molecules from its natural occurrence and environment (solid, liquid, gaseous) to the sensor material itself (mostly liquid phase). See FIG. 1, Scheme 1.

However, FNA receptors have to react specifically only with the derivatized analytes. They should not show any or at least a significantly reduced sensitivity against the non-derivatized analytes or the derivatization molecules itself.

Surprisingly, as the alikeness between the molecules after derivatization significantly increases the specificity of recognition with FNAs also significantly increases because of increased chemical and physical interactions strength. This contradicts with traditional detection methods, where alikeness of molecules, in fact, reduces the specificity of recognition.

Moreover, reference is made to the following examples, which are given to illustrate, not to limit the present invention.

EXAMPLES a) Analytes/small molecules in accordance with the present invention are molecules with low molecular weight (preferably in the range of from 1-500 Da, more preferably in the range from 10-300 Da and most preferably in the range of 50-250 Da) and having first functional groups classified as:

Aliphatic or aromatic prim. or sec. mono, di, tri amines
Aliphatic or aromatic mono, di, tri thiols
Aliphatic or aromatic mono, di, tri alcohols
Aliphatic or aromatic mono, di, tri ketones
Aliphatic or aromatic mono, di, tri aldehydes
Aliphatic or aromatic mono, di, tri carboxylic acids
Aliphatic or aromatic mono, di, tri carboxylic ester
Aliphatic or aromatic mono, di, tri ether
Aliphatic or aromatic mono, di, tri epoxides
Aliphatic or aromatic mono, di, tri halides
and mixtures thereof.
Derivatization agents can be for example:
Substituted aldehydes, iso-thiocyanates, activated esters
Substituted maleimides, iodoacetamides, subst. phenylmercury compounds
Dichlorotriazines, Hydrazines, Hydroxylamines
Ortho-dialdehydes A typical example of the derivatization of an analyte molecule is the reaction between primary amines and aromatic aldehydes forming a schiffs base (see FIG. 1, Scheme 2).

The substituent's structure of the derivatization agents allows a specific interaction with the FNA molecules in order to maximize signal transduction. This can be achieved by base stacking or hydrogen bonding.

Substituents can be, e.g.:

Mono- or polycyclic aromates and heteroaromates like pyridines, purines, pyrimidines, benzofuranes, benzimidazoles, indoles, benzoxazoles, indazoles and derivates thereof.
Aromatic amines, amides carboxylic acids, and
small peptides containing tyrosine, tryptophan, phenylalanine.

Furthermore, in accordance with the present invention, the enzymes (RNase, DNase) responsible for the rapid breakdown of RNA/DNA are excluded from areas where the recognition unit is interacting with the analyte molecules. RNase for example has a molecular size of 40-80 kDa whereas the designated analytes will have sizes not larger than 50-10,000 Da. Several techniques already exists to separate mixtures of molecules comprising a large size distribution. E.g. thin porous polymeric membranes (ethylcellulose) are widely used for protein purification to remove small molecules from protein solutions. Connected upstream of the FNA comprising receptor unit, these membranes must have the capability to separate the analytes from enzymatic active molecules and prevent the rapid degradation of FNA based sensor molecules (see FIG. 1, scheme 3).

The polymeric membranes may be made of at least one of the following materials: cellulose, methylated cellulose, crosslinked dextran, cellophane, polytetrafluoroethylen, polyamide, polyethersulfone, polypropylene, zeolites, or aluminum oxide or other similar materials.

Moreover, an electrochemical signal readout is used in accordance with the present invention to overcome the complex system setup necessary for fluorescence detection. For this reason a stem-loop forming DNA with a specific restriction site for DNAzyme mediated cleavage bearing intercalating and redox-active compounds is used together with negatively charged electrodes. In the non cleaved state the negative charged stem-loop forming DNA loaded with redox-active compounds is repelled from the negative charged surface of the electrode and no signal will be detected. Cleavage by analyte activated DNAzyme will free the redox-active intercalators and a redox reaction at the electrode surface will generate the readout signal (see FIG. 3, Scheme 5). As DNAzymes have a multiple turnover activity, many intercalates bearing stem-loop forming DNAs can be cleaved per single analyte activated DNAzyme (see FIG. 2, Scheme 4). This significantly increases readout signal by amplification and finally increase sensor sensitivity.

Examples of useful DNAzymes are:
8-17 DNAzyme
10-23 DNAzyme
Examples of intercalating, redox-active compounds are:
Methylene blue
Cyanine derivates
Acridine derivates
Ethidium bromide
Propidium iodine
Hydroxystilbamidine derivates
Anthraquinone derivates
Bis-benzimide derivates like Hoechst 33258, 33342, 34580
Ferrocenyl naphthalene diimide
Daunomycin
Anthraquinone disulfonic acid
$Co(bpy)_3^{3+}$
$Co(phen)_3^{3+}$.
Examples of useful electrode materials are:
Metal oxide ($ZnO$, $SnO_2$, $TiO_2$ . . . ), Metals (Au, Ag, Pt, Pd . . . ), Conductive polymer (Carbon paste, Polyaniline, Polypyrrole, Polythiophene)

Figure 4:
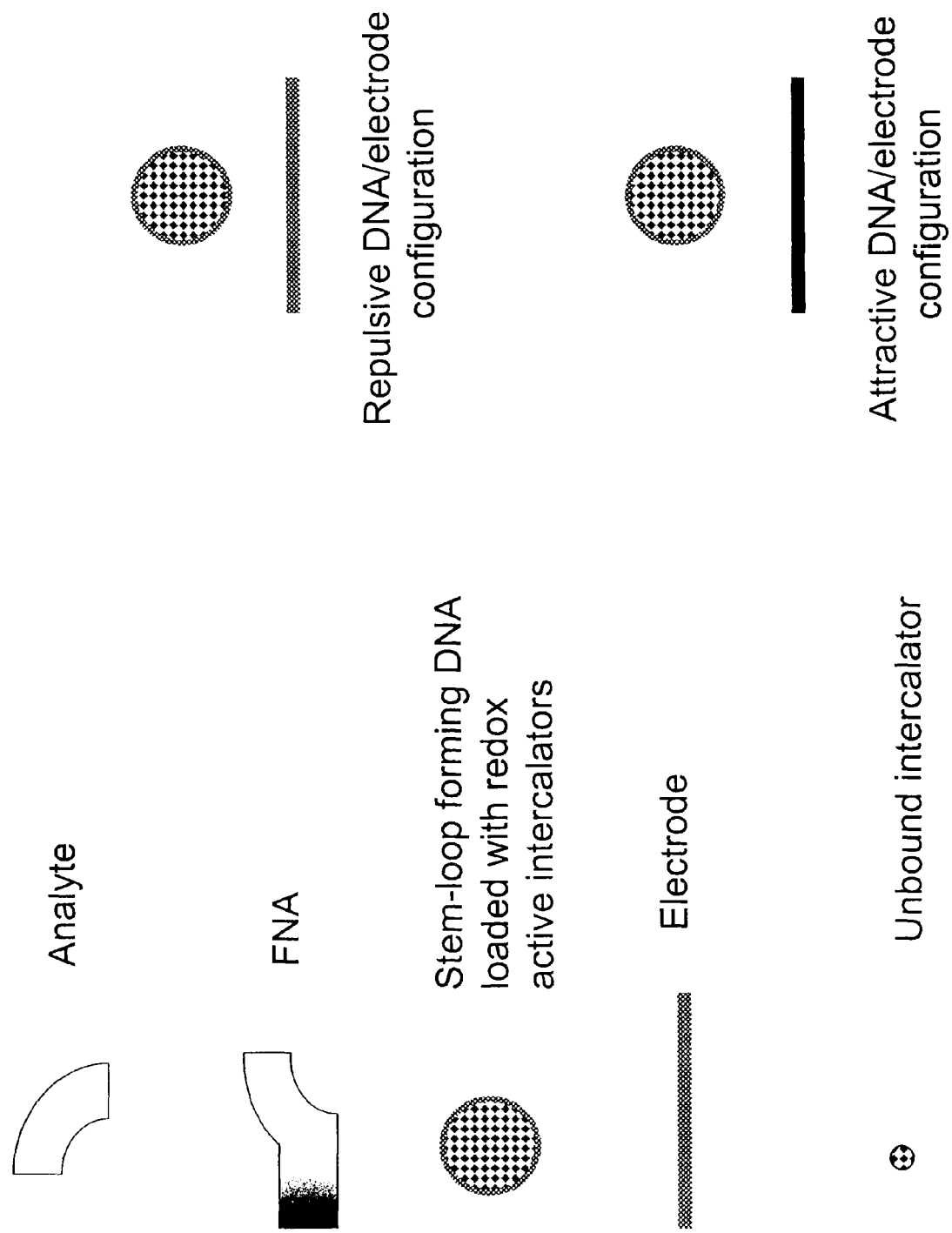
FIG. 4 provides a key for the graphic elements used in FIGS. 5 and 6.
Figure 5:
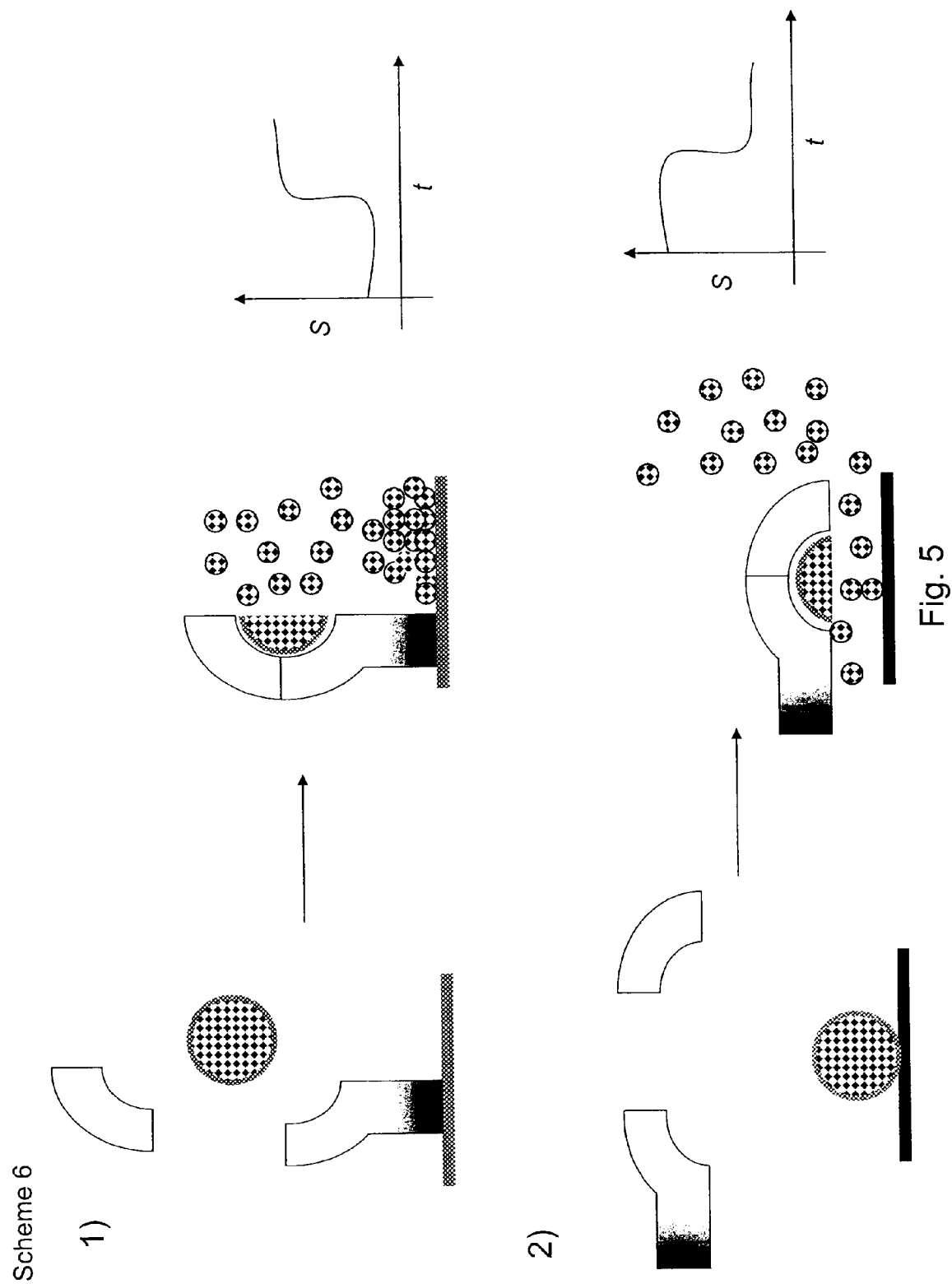
FIG. 5 (Scheme 6) shows embodiments (1) and (2) of various configurations of a sensor in accordance with the present invention, whereas the stem-loop forming DNA loaded with intercalator and the electrode surface can either have a repulsive or an attractive interaction.
Figure 6:
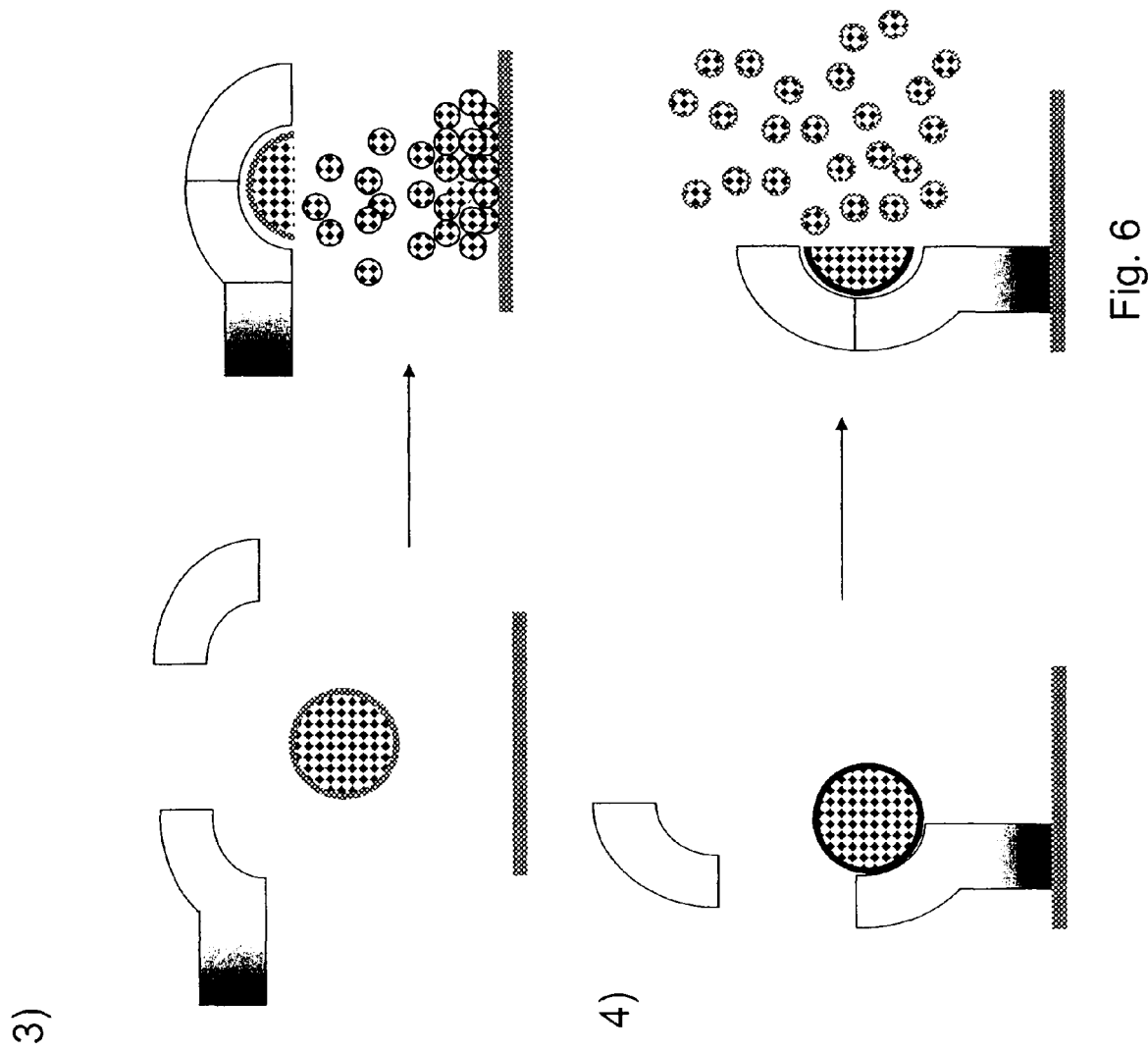
FIG. 6 (Scheme 6) shows embodiments (3) and (4) of various configurations of a sensor in accordance with the present invention, whereas the stem-loop forming DNA loaded with intercalator and the electrode surface can either have a repulsive or an attractive interaction.

Embodiments of possible sensor configurations in accordance with the present invention are:

For signal transduction 4 configurations of the sensor elements are possible (see FIGS. 4-6, Scheme 6). Two of them have a "signal on" architecture and the other two a "signal off" architecture.

FNA is bound to the electrode surface. Derivatized analyte and stem-loop forming DNA loaded with redox active intercalators are in solution. Signal from the intercalators are suppressed due to sterically or electrically hindrance between electrode and stem-loop forming DNA. After FNA activation, redox active intercalators are released and an increase of signal is detectable due to chemi- or physisorption of the intercalator molecules onto the electrode (signal on) (1) (FIG. 5).

Stem-loop forming DNA loaded with redox active intercalators are bound to the electrode surface (by chemi- or physisorption). Derivatized analyte and FNA are in solution and upon FNA activation, redox active intercalators are released and a decrease of signal is detectable at the electrode (signal off) (2) (FIG. 5).

FNA, derivatized analyte and stem-loop forming DNA loaded with redox active intercalators are in solution. Signal from the intercalators are suppressed due to sterically or electrically hindrance between electrode and stem-loop forming DNA. Upon FNA activation, redox active intercalators are released and an increase of signal is detectable due to chemi- or physisorption of the intercalator molecules onto the electrode (signal on) (3) (FIG. 6).

FNA and stem-loop forming DNA loaded with redox active intercalators are chemi-or physisorbed to the electrode. Upon FNA activation, redox active intercalators are released and a decrease of signal is detectable at the electrode (signal off) (4) (FIG. 6).

The method and the sensor in accordance with the present invention provides a unique methodology to make small molecules amenable to nucleic acid based sensor detection. It also allows the possibility to trace small molecules with nucleic acid based sensors in complex environments (gas phase, liquid phase) with high sensitivity and selectivity. Moreover, the present invention allows to design sensor strategies which can be adapted to many analytes. It furthermore inhibits nucleic acid degradation by including a size exclusion process. The signals in accordance with the present invention are enhanced using the specific derivatisation technology and amplification through the use of stem-loop forming DNA-like second nucleic acids and subsequent electrochemical detection.

The features of the present invention disclosed in the specification, the claims and/or in the accompanying drawings, may, both separately, and in any combination thereof, be material for realizing the invention in various forms thereof.

The invention claimed is:

1. A sensor for detection of a derivatized analyte, comprising a detection compartment comprising:
 a) a first nucleic acid capable of specifically recognizing and binding said derivatized analyte, said first nucleic acid comprising:
  an activatable enzyme domain, said enzyme domain, in an active state, having a site specific cleavage activity on nucleic acids,
  an analyte binding domain capable of specifically recognizing and binding said derivatized analyte,
  a communication domain linking said activatable enzyme domain and said analyte binding domain,
  wherein said activatable enzyme domain is activated from an inactive to an active state upon binding of said analyte to said analyte binding domain;
 b) a set of at least a first and second electrode attachable to a power supply; and
 c) a second nucleic acid having a partially double stranded structure and comprising an intercalating, redox-active compound capable of binding to said second nucleic acid, which compound either is electrochemically detectable in its unbound form and is electrochemically not detectable in its bound form, or said compound is electrochemically detectable in its bound form and is electrochemically not detectable in its unbound form, wherein said second nucleic acid further comprises a cleavage site recognized by said enzyme domain of said first nucleic acid in its active state, and wherein, upon cleavage of said cleavage site, said intercalating, redox-active compound, when bound to said second nucleic acid, becomes released from said second nucleic acid, wherein said sensor specifically recognizes said derivatized analyte by the first nucleic acid a) specifically recognizing and binding said derivatized analyte;

the sensor further comprising a separation compartment located upstream of said detection compartment and separated from said detection compartment by a polymeric semipermeable membrane that excludes RNAse and other molecules having a molecular weight >10,000 Da and responsible for the rapid breakdown of RNA and/or DNA and which permits the passage of molecules of the derivatized analyte to pass from said separation compartment to said detection compartment, wherein said first nucleic acid binds to a derivatised analyte that is produced by reacting a starting analyte and a derivatisation agent to form said derivatised analyte, wherein:

said starting analyte comprises a first functional group;

said derivatisation agent comprises a second functional group;

said first functional group and said second functional group are capable of reacting with each other to form a bond between said starting analyte and said derivatisation agent; and said derivatisation agent further comprises a substituent allowing for base stacking or hydrogen bonding between said derivatisation agent and a nucleic acid, and wherein said starting analyte is a molecule having a molecular weight in the range of from 50 to 250 Da and wherein said derivatised analyte has a molecular weight in the range from 250 to 2,000 Da.

2. The sensor of claim 1, wherein said first nucleic acid is a DNAzyme.

3. The sensor of claim 1, wherein said second nucleic acid is a stem-loop forming DNA probe.

4. The sensor of claim 1, wherein said intercalating, redox-active compound is at least one selected from the group consisting of methylene blue, a cyanine derivative, an acridine derivative, ethidium bromide, propidium iodine, a hydroxystilbamidine derivative, an anthraquinone derivative, a bis-benzimide derivative, ferrocenyl naphthalene diimide, daunomycine, anthraquinone disulfonic acid, $Co(bpy)_3^{3+}$, and $Co(phen)_3^{3+}$, wherein "bpy" is bipyridine and "phen" is 1,10 phenanthroline.

5. The sensor of claim 1, wherein said sensor satisfies a condition selected from the group consisting of:

a) said first nucleic acid is bound to a surface of at least one of said electrodes, said second nucleic acid is in a solution covering, contacting or surrounding said surface, wherein, for detecting, a sample is added to said solution;

b) said second nucleic acid is bound to a surface of at least one of said electrodes, said first nucleic acid is in a solution covering, contacting or surrounding said surface, wherein, for detection, a sample is added to said solution;

c) said first and said second nucleic acid are in a solution covering, contacting or surrounding a surface of at least one of said electrodes, wherein, for detection, a sample is added to said solution; and d) said first and said second nucleic acid are bound to a surface of at least one of said electrodes, wherein, for detection, a sample is added so as to contact said surface.

6. The sensor of claim 1, wherein said semi permeable membrane comprises at least one of cellulose, methylated cellulose, dextran, cellophane, polytetrafluoroethylen, polyamide, polyethersulfone, polypropylene or a zeolite, aluminum oxide, or a combination thereof.

7. The sensor of claim 1, wherein said first functional group of said starting analyte is selected from at least one group consisting of a phenyl, an alcohol, a ketone, an aldehyde, a carboxylic acid, a carboxylic ester, an ether, an epoxide, a thiol, an amine, an amide and a halide.

8. The sensor of claim 1, wherein said second functional group of said derivatisation agent is at least one selected from the group consisting of an aldehyde, an iso-thiocyanate, an activated ester, a maleimide, an iodoacetamide, a phenylmercury group, a triazine, a hydrazine, a hydroxylamine, and a dialdehyde.

9. The sensor of claim 1, wherein said substituent of said derivatisation agent is at least one selected from the group consisting of a pyridine, a purine, an aromatic amine, an amide, a carboxylic acid, a peptide comprising tryptophan, a peptide comprising tyrosine, and a peptide comprising phenylalanine.

10. A sensor that detects a small derivatized analyte that has a molecular weight ranging from 200 to 2,000 Da that comprises:

(i) a detection compartment containing a first nucleic acid that binds to the small derivatized analyte, wherein said first nucleic acid contains (a) a binding domain that specifically binds to the small derivatized analyte, (b) a communication domain linking the binding domain (a) and the enzyme domain (c), and (c) an enzyme domain that when activated by the binding of the small derivatized analyte to the binding domain cleaves a specific site on a second nucleic acid sequence, (ii) a partially double-stranded second nucleic acid that is bound to an intercalating, redox-active compound, and that contains a cleavage site recognized and cleaved by the enzyme domain (c) of the first nucleic acid sequence, wherein said second nucleic acid when cleaved by the enzyme domain (c) of the first nucleic acid sequence releases the intercalating, redox-active compound;

(iii) a separating compartment separated from the detection compartment by a semipermeable polymeric membrane that permits passage of the small derivatized analyte that has a molecular weight ranging from 200 to 2,000 Da from the separating compartment to the detection compartment and which retains molecules having a molecular weight greater than 10,000 Da thus excluding them from the detection compartment;

wherein said first nucleic acid in detection compartment (i) recognizes a derivatized analyte that is produced by reacting a starting analyte having a molecular weight ranging from 200 to 250 Da with a derivatization agent, wherein the starting analyte comprises a first functional group and the derivatisation agent comprises a second functional group and the first functional group and said second functional group reacting with each other to form a bond between said starting analyte and the derivatisation agent; and wherein said derivatisation agent further comprises a substituent allowing for base stacking or hydrogen bonding between said derivatisation agent and the first nucleic acid.

11. The sensor of claim 10, wherein the small derivatized analyte is a derivatized small charged, non-polar organic or inorganic molecule, and wherein the first nucleic acid recognizes said derivatized analyte.

12. The sensor of claim 10, wherein the first nucleic acid sequence is a DNAzyme.

13. The sensor of claim 10, wherein the second nucleic acid sequence is a stem-loop forming DNA probe that contains a cleavage site recognized by the first nucleic acid.

14. The sensor of claim 10, wherein the intercalating redox-active agent is electrochemically detectable when it is not bound to the second nucleic acid sequence and not detectable when bound.

15. The sensor of claim 10, wherein the intercalating redox-active agent is electrochemically detectable when it is bound to the second nucleic acid sequence and not detectable when bound.

16. The sensor of claim 10, wherein the first nucleic acid is bound to the surface of an electrode and the sensor is configured so as to permit a second nucleic acid in a solution containing the derivatized analyte to cover, contact or surround the surface of the electrode.

17. The sensor of claim 10, wherein the second nucleic acid is bound to the surface of an electrode and the sensor is configured so as to permit a first nucleic acid in a solution containing the derivatized analyte to cover, contact or surround the surface of the electrode.

18. The sensor of claim 10, wherein the first and second nucleic acid are bound to the surface of an electrode and the sensor is configured so as to permit a solution containing the derivatized analyte to cover, contact or surround the surface of the electrode.

19. The sensor of claim 10, wherein the surface of an electrode is configured so as to permit a first nucleic acid, second nucleic acid, and derivatized analyte in a solution to cover, contact or surround the surface of the electrode.

* * * * *

SEQUENCE LISTING

<160> NUMBER OF SEQ ID NOS: 2

<210> SEQ ID NO 1
<211> LENGTH: 57
<212> TYPE: DNA
<213> ORGANISM: Artificial
<220> FEATURE:
<223> OTHER INFORMATION: DNAzyme

<400> SEQUENCE: 1
gcgtccttca gagagagtgg gtgcttttgc acccaggcta gctacaacga ctctctc      57

<210> SEQ ID NO 2
<211> LENGTH: 21
<212> TYPE: DNA
<213> ORGANISM: Artificial
<220> FEATURE:
<223> OTHER INFORMATION: stem-loop forming DNA
<220> FEATURE:
<221> NAME/KEY: misc_feature
<222> LOCATION: (11)..(12)
<223> OTHER INFORMATION: RNA residue

<400> SEQUENCE: 2
cctgagagag augggtgcag g                                              21